United States Patent
Chavan et al.

(10) Patent No.: US 6,376,701 B1
(45) Date of Patent: Apr. 23, 2002

(54) PROCESS FOR THE TRANSESTERIFICATION OF KETO ESTERS USING SOLID ACIDS AS CATALYSTS

(75) Inventors: Subhash Prataprao Chavan; Shubhada Wasudeo Dantale, both of Maharashtra; Alive Keshavaraja, Karnataka; Arumugamangalam Venkataraman Ramaswamy, Maharashtra; Puduklatan Kadar Zubaidha, Madras, all of (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 08/643,941

(22) Filed: May 7, 1996

(30) Foreign Application Priority Data

Dec. 29, 1995 (IN) ................................................ 2478/95

(51) Int. Cl.$^7$ ............................................... C07L 69/72
(52) U.S. Cl. ....................................... 560/174; 560/174
(58) Field of Search ................................. 560/178, 174

(56) References Cited

U.S. PATENT DOCUMENTS 2,412,928 A * 12/1946 Tuerck et al. ............... 260/483
2,533,015 A * 12/1950 Jasion et al. ................... 71/2.4
2,843,623 A * 7/1958 Hansley et al. ............. 260/483
4,825,008 A * 4/1989 Gunther et al. ............. 568/391

OTHER PUBLICATIONS

Chavan et al., "Use of Solid . . . Ketoesters", Tetrahedron Letters, vol. 37, No. 2, pp. 233–236, Jan. 1996.*

Gilbert et al., "Transesterification of 3–Oxo . . . Alcohols", J. Org. Chem., vol. 53, No. 2, pp. 449–450, Jan. 1988.*

* cited by examiner

Primary Examiner—Rosalynd Keys
(74) Attorney, Agent, or Firm—Michael D. Bednarek; Shaw Pittman LLP

(57) ABSTRACT

A process for the transesterification of keto esters and alcohols in approximately stoichiometric amounts using a solid acid catalyst. Solid acid catalysts may be sulfated zirconia, sulfated tin oxide, sulfated titania, sulfated iron oxide, heteropoly acids, acidic clays, acidic zeolites, or any other solid acids with high acidity or super acidity, with or without dopants. One equivalent or more of keto ester, one equivalent or more of alcohol, the solid acid catalyst, and an appropriate solvent are mixed and heated to 70 to 120° C. at atmospheric or reduced pressure to furnish the keto transester in high yields.

16 Claims, No Drawings

PROCESS FOR THE TRANSESTERIFICATION OF KETO ESTERS USING SOLID ACIDS AS CATALYSTS

The present invention relates to a process for the transesterification of keto esters. More particularly, the present invention relates to a process for the trans esterification of ketoesters using solid acids as catalysts. The solid acids used in the present invention may be either sulfated zirconia, sulfated tin oxide, sulfated titania, sulfated iron oxide, any heteropoly acid, acidic clay, acidic zeolite, like H-ZSM 5, HY, etc. or any other solid acid with high acidity or super acidity. The process for the preparation of the solid acids has been fully described in our co-pending U.S. patent application Ser. No. 08/653,171 filed May 24, 1996, which includes the following disclosure.

The present invention relates to an improved process for the preparation of sulphated mixed metal oxides. More particularly, the present invention relates to a process for the preparation of sulfated mixed metal oxides having the general formula $M_xN_{1-x}O_2$ where M is one of the group IIIB metals such as yttrium, scandium or lanthanum and N may be either Zr, Ti or Sn and 'x' may vary from 0.01 to 0.4. The sulphated mixed metal oxides termed as solid acids or super acids or modified super acids, prepared according to the process of the present invention is useful as a catalyst for various organic transformations such as, trans esterification, Diels-Alder reactions, Eno reactions etc.

Solid acids are well known in the field of catalysis since the pioneering work of G. A. Olah, who developed strong liquid acids such as sulphuric acid, aluminum chloride etc., (G. A. Olah, U.S. Pat. No. 4,116,880, 1970) later on replaced by solid superacids such as sulphated zirconia, sulphated titania etc. Several modifications of such solid acid materials have been attempted in the prior art recently. Hsu et al., reported that Fe & Mn promoted sulphated zirconia catalyst shows higher stability than pure sulphated zirconia and that this new catalyst can isomerize n-butane at near room temperature with a rate three orders of magnitude greater than sulphated zirconia (E. J. Hollstein, J. T. Wei and C. Y. Hsu, U.S. Pat. No. 4,918,041 (1990). Apart from this there are several other isomerization reactions promoted by solid super acids. For example, Kramer [U.S. Pat. No. 4,357,484 (1984)] disclosed an isomerization process where adamantine is added to a halide containing Lewis acid catalyst and it appears that carbonium intermediate must be generated in solution to effect the isomerization reaction. A process for the isomerization of cyclic hydrocarbons using liquid acids such as sulfuric acid or fluoro sufonic acid in the presence of adamantine has been described in U.S. Pat. No. 3,871,598 (1972).

There are several other areas in the field of chemistry where these superacids or modified superacids finds applications. A mention must be made here of industry application of solid acids as catalysts in catalysing alkylation, dewaxing, fluidized catalytic cracking, hydrocracking, hydrotreating, isomerization and reforming, Beckman rearrangement, Fries rearrangement etc.

Attempts have also been made in the prior art to use solid acids for catalysing Diels-Alder reactions/cyclo-additions, and other allied reactions using several Lewis acids such as $TlCl_4$, $SnCl_2$, $ZnCl_2$ (complexed with ethers), $ZnBr_2$, $BF_3$, Eu(III) complexes, YB(III), Sc(III) and XI(III) complexes. However, there are several limitations in using these as catalysts because of poor endo product selectivity, difficulty in recovery of the catalyst, handling problems and lack of reusability.

In view of the above mentioned limitations of the prior art process it was desirable to develop some solid acid catalysts which have properties similar to that of the known liquid super acids or lewis acid anchored with metal complexes, which not only possess high acidity but also have stable structure and useful in various organic transformations.

The objective of the present invention is therefore to develop a solid acid capable of being used as a catalyst in C—C bond forming reaction, which is active either at room temperature or at a higher temperature, easy to recover, reusable, and selectively in synthesis of endo products in Diles-Alders reactions.

The present invention relates to preparation of a family of stable solid acids which may also be designated as solid solutions the surface of which are modified with sulfates, having very high acidity and they can be identified as "Superacidic Solid Solution"(SSS). The "SSS" possesses strong Lewis acidity and also Bronsted acidity to some extent as demonstrated by infra red spectra of adsorbed pyridine and Temperature Programmed Desorption of Ammonia and potentiometric titration of n-butylamine in nonaqueous media.

Accordingly, the present invention provides a process for the preparation of sulphated metal oxides which comprises:
a) preparing an aqueous solution A of one of the metal salts of zirconium, tin, titanium or iron the strength of which ranging from 0.1 to 2 M,
b) preparing an aqueous solution B of group III B metal salts (such as metal salts or yttrium, scandium or lanthanum) the strength of which ranging from 0.1 to 2 M,
c) mixing solutions A and B in the molar ratio of P:Q where, p ranging from 99 to 60 and q ranging from 1 to 40 and p+q always being equal to 100, to form solution C,
d) precipitating solution C to form hydroxide D by adding ammonium hydroxide or tetraalkyl ammoniumhydroxide where, the alkyl group is selected from methyl, ethyl, propyl or butyl, drying the precipitate D formed at a temperature ranging from 90 to 110° C. to form a dry powder designated as E,
e) treating the powder E with sulfuric acid or ammonium sulfate of strength ranging from 0.1 to 4 M for a period ranging from 1 to 12 hours followed by heating the resulting product at a temperature ranging between 40 to 110° C. at atmospheric pressure, or also at reduced pressure to get a dry powder designated as F,
f) calcining the dry powder F at a temperature ranging from 300 to 500° C. for 3 to 12 hours to get sulphated metal oxides catalyst.

In the preferred embodiment of the present invention, such superacidic solid solution mainly consists of one among the zirconia, titania, tin oxide or iron oxide in major amount, (hereinafter called 'support metal oxide') and may contain at least one or all of the group IIIb rare earth metals like scandium, yttrium or Lantahnum (hereinafter called "dopant metaloxide") and the support metal oxide forms solid solution with dopant metaloxide(s) when the latter is co-precipitated or co-gelated with the former followed by calcination.

In another embodiment of the present invention, the support metal oxide is treated with stabilizing anions preferably sulfates before calcination, while the source of sulfates are from $SO_2$, $SO_3$, $H_2S$, $H_2SO_4$, or ammonium sulfate and the amount of sulfates may range between 0.1 to 4% (weight % as sulfates) of the total weight of the catalyst.

In yet another embodiment of the present invention, the superacidic solid solution have general formula, $M_xN_{1-x}O_2$ where x may range from 0.1 to 0.40 which means amount of dopant metal oxide content may vary from 1 to 40 mole % and amount of support metaloxide content may vary from 99 to 60 mole %. In other words, in the extreme cases, it may either have merely support oxide doped with sulphates in which case it can be conveniently called as "superacids" instead of the name "superacidic solid solution" or it may also have separate phases of support and dopant oxides in which case it may be called as "superacidic mixed oxides."

According to one feature of the present invention, the source of the group III B metal oxide may be from their respective salts such as nitrates, chlorides, acetates, or sulphates or their alkoxides. For example it may be either Yttrium nitrate, Scandium nitrate, Lanthanum acetate, Lanthanum chlorides, etc.

According to another feature of the present invention, the source of sulphates may also be gases such as $SO_3$ or $SO_2$ in which case the powder D is exposed to these gases for time ranging from 3 to 24 hours.

The catalysts prepared according to the process of the present invention is active in catalysing reactions such as—C coupling reaction (Diels-Alders reaction or Hetero-Diels-Alders reaction or inverse electron demand Diels-Alders reaction or one reaction), transesterification and protection of carbonyl groups and deprotection of allyl esters. Some of these processes are described in our co-pending patent application No. NF 175/95 and NF 177/95.

The process of the present invention is further described with following examples which are for illustrative purpose only and should not be construed to limit the scope of the present invention.

EXAMPLE A

In this example, preparation of sulphated zirconia doped with yttria as promotor is described.

An aqueous solution of zirconyl nitrate was prepared by weighing 38.85 g of zirconyl nitrate and adding 250 ml of deionised water under constant stirring to get a clear solution, (solution A).

An aqueous solution of yttrium nitrate was prepared by weighing 11.68 g of ytrium nitrate and adding 50 ml of water under constant stirring to get a clear solution, (solution B).

Solution A and B are mixed together and stirred for 1 hour to get a homogeneous mixture (solution C).

50 ml of aqueous ammonium hydroxide was then added to solution C with vigorous stirring at a pH of 8.5 to get a white coloured precipitate, which was filtered and washed 10 times with deionised water to remove the residual ammonia and dried at 110° C. for 12 hours to get a dry powder (D).

5 g of the powder D was then taken in a 100 ml flask and 26 ml of 2N sulphuric acid was added under constant stirring and it was kept at 75° C. until evaporation to get a dry powder, E.

The powder E was then dried at 110° C. for 6 hours and subsequently calcined at 450° C. for 4 hours to get sulphated zirconia catalyst doped with yttria in the final form where the molar ratio of Zr and Y were found to be 84:16.

The acidic properties of the catalyst prepared according to the above procedure is illustrated by means of various physico-chemical techniques such as XRD, FTIR, potentiometric titration, temperature programmed desorption (TPD), SEM and $N_2$ adsorption techniques. The X-ray powder diffraction profile of the catalyst showed the formation of the cubic phase. The IR spectra of the pyridine adsorbed on the catalyst is represented in the FIG. 1 of the drawings accompanying the specification. From the FIG. 1 it can be seen that the IR spectra shows absorption bands at 1640, 1605, 1577, 1542, 1490 and 1444 $cm^{-1}$. The strong absorption band at 1440 $cm^{-1}$ indicates the presence of the coordinated pyridine on the Lewis acid sites of the catalyst. The presence of the few Bronsted acid sites are indicated by the absorption band at 1542 $cm^{-1}$ of the pyridinium ion. The potentiometric titration curves of the present catalyst compared to that of the sulfated zirconia catalyst without the yttria dopant is compared in the FIG. 2. The potentiometric titrations of the acid sites with n-butylamine in non-aqueous medium shows the influence of yttria in enhancing the number of acid sites. Further support for the strong acidity or superacidity of the present catalyst composite. is illustrated by the temperature programmed desorption (TPD) of ammonia adsorbed on the catalyst the profile of which is depicted in the FIG. 3. The presence of very strong acid sites in the present catalyst is indicated by the peak maxima at 530° C. in the TPD profile. The BET surface area of the catalyst is found to be 150 $m^2$ $g^{-1}$. The lattice defect due to the incorporation of the yttrium in the lattice of zirconia appears to enhance the number and strength of the Lewis acidity of the catalyst.

EXAMPLE B

This example describes the preparation of sulphated zirconia doped with lanthana as promoter is described.

An aqueous solution of zirconyl nitrate was prepared by taking 0.85 moles of zirconyl nitrate and adding 250 ml of deionized water under constant stirring to get a clear solution, (solution A).

An aqueous solution of lanthanum nitrate was prepared by taking 0.15 moles of yttrium nitrate and adding 50 ml of water under constant stirring to get a clear solution, (solution B).

Solution A and B are mixed together and stirred for 1 hour to get a homogeneous mixture (solution C).

50 ml of aqueous ammonium hydroxide was then added to, solution C with vigorous stirring at a pH of 8.5 to get a white coloured precipitate, which was filtered and washed 10 times with deionized water to remove the residual ammonia and dried at 110° C. for 12 hours to get a dry powder (D).

5 g of the powder D was then taken in a 100 ml flask and 25 ml of 211 ammonium sulphate was added under constant stirring and it was kept at 75° C. until evaporation to get a dry powder, E.

The powder E was then dried at 110° C. for 6 hours and subsequently calcined at 450° C. for 4 hours to get sulphated zirconia catalyst doped with lanthana, the chemical composition of which was found to be 83.5 mole % Zr, 14.7 mole % La and 1.8 mole % S.

EXAMPLE C

In this example, preparation of sulphated tin oxide without any dopant metal oxide is described.

An aqueous solution of stannous chloride is prepared by adding 50 g of stannous chloride to 500 ml of water under constant stirring, to get a solution A. The resultant solution was then precipitated as hydroxide by adding 50 ml of etramethyl ammonium hydroxide (25% aqueous) with vigorous stirring at a pH of 8.5 to get a yellow coloured precipitate which was filtered and washed 10 times with deionised water to remove the residual ammonia and dried at 110° C. for 12 hours to get a dry powder D.

About 5 g of the powder D was then taken in a 100 ml flask and 25 ml of 2N sulphuric acid was added under constant stirring and it was kept at 75° C. until evaporation to get a dry powder, E.

The powder E was then dried at 110° C. for 8 hours and subsequently calcined at 450° C. for 4 hours to get sulphated tion oxide catalyst in the final form.

Returning to the disclosure of the present invention, the keto esters used.

The Keto esters used in the process of the present invention may be either α-keto esters, β-keto esters, or γ keto esters but preferably β-keto esters.

Transesterification is an equilibrium driven process where an ester is transformed into another ester through interchange of alkoxy moiety. $RCOOR'+R"OH=RCOOR"+R'OH$, where R may be any alkyl group or aryl group, R' may be either an alkyl or an aryl group, and R" may be an alkyl group or an allyl group. The above mentioned reaction is one of the ideal organic reactions that have seen enormous laboratory uses and industrial applications. Transesterification is more advantageous than ester synthesis from carboxylic acids and alcohols. This is mainly due to the solubility limitations of carboxylic acids in organic solvents whereas the esters are commonly soluble in most of the organic solvents. Apart from its applicability in pure organic synthesis, transesterification is also useful in many other areas such as polymerization, i.e., ring opening of lactones, in paint industry for curing of alkyl resins, and in cosynthesis of ethylene glycol and dimethylene carbonate from ethylene carbonate and methanol.

In the prior art, although the reaction is known to occur by simply mixing the two components, these equilibrium driven reactions often require an excess of one of the reactants to obtain good yields (above 80%) of the desired products. It has long been known that the reaction is accelerated by acid or base catalysts. Traditionally most often used, acid catalysts include sulfuric acid, sulfonic acid, hydrochloric acid and phosphoric acid. In a typical procedure of transesterification known in the prior art, a mixture of an ester and alcohol together with a catalytic amount of sulfuric acid were subjected to distillation. The base catalysts known in the prior art include a wide variety of metal alkoxides such as potassium alkoxides, sodium alkoxides, lithium alkoxides or titanium alkoxides, metal acetates or metal carbonates.

The process for the transesterification known in the prior art however suffers from following limitations.
1) The catalysts are difficult to handle because of the corrosive and volatile nature of the liquid catalysts.
2) Base catalysts such as metal alkoxides are costly.
3) Most of the known acid and base catalysts are hazardous.
4) In most of the cases, the reaction is homogeneous and separation of the reaction products from the catalyst is tedious.
5) Almost all the reported reactions are equilibrium driven where an excess of alcohol or ester is employed to drive the equilibrium in the desired direction.

The main objective of the present invention is therefore to provide an improved process wherein the transesterification reaction is effected in the presence of a catalyst which overcomes all the above limitations. The strategy in selecting the catalyst in the present process is that the catalyst is acidic, solid and not hazardous.

The process of the present invention consists of the transesterification reactions of various keto esters in heterogeneous media using corresponding alcohols in the presence of one or more of the solid acids mentioned above. The keto esters used in the process of the present invention may be preferably either β keto ester or β keto esters such as methyl acetoacetate, ethyl acetoacetate, cyclopentenone, methyl levulinate, aryl keto esters or any other alkyl keto esters. The alcohols used in the process of the present invention may be one of the open chain alcohols, cyclic alcohols, aromatic alcohols, allylic alcohols including chiral alcohols.

Accordingly, the present invention provides a process of the transesterification of keto esters which comprises: mixing 1 equivalent or more of a correspoonding keto ester, 1 equivalent or more of an appropriate alcohol, and a solid acid catalyst (5 to 30% by weight of keto ester) in a solvent such as toluene, followed by heating to a temperature ranging from 70 to 120° C. at atmospheric or reduced pressure, in a suitable flask provided with a distillation condenser to remove solvent by condensation.

According to one embodiment of the present invention, the solid acid catalysts may or may not have sulfate loadings. The extent of sulfation also may vary in the range of 0.1% to 10%. The solid acid catalysts may or may not have group IIIB metal oxides such as yttria, scandia or lanthana as dopants.

According to another embodiment of the process of the present invention, the amount of catalyst used may range from 5% by weight to 30% by weight of the keto ester.

According to yet another embodiment of the process of the present invention, the reaction is monitored by thin layer chromatography (TLC) and after ensuring the completion of the reaction, the catalyst is filtered off and the filtrate concentrated and chromatographed on a silica gel column (95:5 petroleum ether: ethyl acetate) to afford the ester as a viscous colorless liquid in excellent yield.

The process of the present invention is further described with reference to the following examples which are illustrative only and should not be construed to limit the scope of the present invention.

EXAMPLE 1

This example describes the procedure to prepare the solid acids catalyst.

To an aqueous solution of 1 mole of stannous chloride, aqueous ammonia (28%) was added with vigorous stirring until a pH of 8 was achieved and the stirring was continued for 6 hours to produce a yellowish precipitate of the hydrous oxide of tin. This was dried at 110° C. for 12 hours to get a dry powder. This dry powder was then treated with 50 ml of 0.5 molar ammonium sulfate solution and heated for 8 hours to evaporate the water. The dry powder was then calcined at 450° C. for 3 hours. A highly acidic material was obtained as confirmed by various physicochemical techniques such as temperature programmed desorption (TPD) of ammonia, infra red spectra of adsorbed pyridine on the catalyst and potentiometric titration of n-butyl amine in non aqueous media.

EXAMPLE 2

A mixture of 1 equivalent of methyl acetoacetate, 1 equivalent of allyl alcohol and 100 mg of sulfated tin oxide catalyst prepared according to example 1, in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford the allyl acetoacetate as a viscous colorless liquid in 90% yield.

EXAMPLE 3

A mixture of 1 equivalent of methyl acetoacetate, 1 equivalent of cyclohexanol and 100 mg of sulfated tin oxide catalyst prepared according to example 1 above, in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford the cyclohexyl acetoacetate ester as a viscous colorless liquid in 85% yield.

EXAMPLE 4

A mixture of 1 equivalent of methyl acetoacetate, 1 equivalent of nbutyl alcohol and 100 mg of sulfated tin oxide catalyst prepared according to the procedure given in example 1 above, in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford the butyl acetoacetate as a viscous colorless liquid in 97% yield.

EXAMPLE 5

A mixture of 1 equivalent of methyl acetoacetate, 1 equivalent of methyl acetoacetate, 1 equivalent of octyl alcohol and 100 mg of sulfated tin oxide catalyst prepared according to example 1 above, in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford the octyl acetoacetate as a viscous colorless liquid in 89% yield.

EXAMPLE 6

A mixture of 1 equivalent of methyl acetoacetate, 1 equivalent of menthol and 100 mg of sulfated tin oxide catalyst prepared according to example 1 above, in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford menthyl acetoacetate as a viscous colorless liquid in 91% yield.

EXAMPLE 7

A mixture of 1 equivalent of methyl acetoacetate, 1 equivalent of cyclohexanol and 100 mg of sulfated tin oxide catalyst prepared according to example 1 above, in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford cyclohexyl acetoacetate as a viscous colorless liquid in 84% yield.

EXAMPLE 8

A mixture of 1 equivalent of methyl acetoacetate, 1 equivalent of chlorohydrin and 100 mg of sulfated tin oxide catalyst prepared according to example 1, in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford 2-chloroethyl acetoacetate as a viscous colorless liquid in 92% yield.

EXAMPLE 9

A mixture of 1 equivalent of methyl acetoacetate, 1 equivalent of tertiary butyl alcohol and 100 mg of sulfated tin oxide catalyst prepared according to example 1, in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford t-butyl acetoacetate as a viscous colorless liquid in 50% yield.

EXAMPLE 10

A mixture of 1 equivalent of methyl acetoacetate, 1 equivalent of 3-phenylpropyl alcohol and 100 mg of sulfated tin oxide catalyst in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford 3-phenylpropyl acetoacetate as a viscous colorless liquid in 97% yield.

EXAMPLE 11

In this example, procedure of transestrification of methyl acetoacetate with 1-phenyl ethanol is described. A mixture of 1 equivalent of methyl acetoacetate, 1 equivalent of 1-phenyl ethanol and 100 mg of sulfated tin oxide catalyst in 20 ml of toluene was heated to 110° C. in a two necked round bottom flask provided with a distillation condenser to remove methanol. The reaction was monitored by thin layer chromatography (TLC). After completion of the reaction (about 6 hours), the catalyst was filtered and the filtrate was concentrated and chromatographed on a silica gel column (95% petroleum ether and 5% ethyl acetate) to afford 1-phenylethyl acetoacetate as a viscous colorless liquid in 97% yield.

Advantages of the process of the present invention include:

1) The solid acids used as catalyst are environmentally friendly, easy to handle, easy to recover from the reaction mixture and are reusable.

2) The process is effective selectively for β and γ keto esters.
3) The process allows the preparation of even tertiary butyl esters in the presence of solid acids which are otherwise difficult to prepare under normal conditions.
4) The process allows the use of allyl alcohols for trans esterification. Further, the presence of molecular sieves in large excess in addition to a stoichiometric amount of DMAP (dimethylamino pyridine) is not mandatory for effective exchange.
5) One equivalent of the ester and one equivalent of alcohol is sufficient to effect the trans esterification in the presence of the catalyst. In the normal reaction, excess usage of one of the reactants is necessary to achieve good yields.

What is claimed is:

1. A process for the transesterification of keto esters comprising, mixing 1 equivalent or more of a keto ester, 1 equivalent or more of an alcohol and a solid acid catalyst in a solvent followed by heating to a temperature ranging from 70 to 120° C. at atmospheric or reduced pressure, wherein the keto ester is at least one keto ester selected from the group consisting of α keto esters, β keto esters, and γ keto esters; the alcohol is at least one alcohol selected from the group consisting of tertiary alcohols, allyl alcohols and aromatic alcohols; and the solid acid catalyst is at least one acid selected from the group consisting of sulfated metal oxides including tin oxide, iron oxide, titanium oxide an zirconium oxide, modified or not by additives or promoters; heteropoly acids; acidic clays; acidic zeolites; acidic ion exchange resins; and mixtures thereof, and wherein the trans esterification is not carried out in the presence of a stoichiometric amount of dimethylamino pyridine.

2. The process as claimed in claim 1 wherein the keto ester is a β-keto ester selected from the group consisting of methyl acetoacetate, ethyl acetoacetate, and hexyl acetoacetate.

3. A process for the trans esterification of keto esters comprising, mixing 1 equivalent or more of a keto ester, 1 equivalent or more of an alcohol and a solid acid catalyst in a solvent followed by heating to a temperature ranging from 70 to 120° C. at atmospheric or reduced pressure, wherein the keto ester is at least one keto ester selected from the group consisting of α keto esters, β keto esters, and γ keto esters; the alcohol is at least one alcohol selected from the group consisting of allyl alcohols and aromatic alcohols; and the solid acid catalyst is at least one acid selected from the group consisting of sulfated metal oxides, wherein the metal oxide may be tin oxide, iron oxide, titanium oxide, zirconium oxide or any other sulfated oxide which may be modified by additives or promoters; heteropoly acids; acidic clays; acidic zeolites; acidic ion exchange resins; and mixtures thereof, wherein the trans esterification is not carried out in the presence of a stoichiometric amount of dimethylamino pyridine.

4. The process as claimed in claim 3 wherein the alcohol is a primary alcohol.

5. The process as claimed in claim 1, wherein the keto ester is a γ-keto ester selected from the group consisting of ethyl levulinate and methyl levulinate.

6. The process as claimed in claim 3, wherein the alcohol is a secondary alcohol.

7. The process as claimed in claim 1, wherein the tertiary alcohol is selected from the group consisting of tertiary butanol, tertiary cyclic alcohols, tertiary aromatic alcohols, tertiary allylic alcohols, and chiral tertiary alcohols.

8. The process as claimed in claim 1, wherein the solid acid catalyst is added in an amount of about 5 to 30% by weight of the keto ester.

9. A process for the trans esterification of keto esters comprising, mixing 1 equivalent or more of a keto ester, 1 equivalent or more of an alcohol and a solid acid catalyst in a solvent followed by heating to a temperature ranging from 70 to 120° C. at atmospheric or reduced pressure, wherein the keto ester is at least one keto ester selected from the group consisting of α keto esters, β keto esters, and γ keto esters; the alcohol is at least one alcohol selected from the group consisting of, allyl alcohols and aromatic alcohols; and the solid acid catalyst is at least one acid selected from the group consisting of sulfated metal oxides, wherein the metal oxide may be tin oxide, iron oxide, titanium oxide, zirconium oxide or any other sulfated oxide which may be modified by additives. or promoters; heteropoly acids; acidic clays; acidic zeolites; acidic ion exchange resins; and mixtures thereof, and wherein the γ-keto ester is selected from the group consisting of ethyl levulinate and methyl levulinate wherein the transesterification is not carried out in the presence of a stoichiometric amount of dimethylamino pyridine.

10. The process as claimed in claim 9, wherein the alcohol is a primary alcohol.

11. The process as claimed in claim 9, wherein the alcohol is a secondary alcohol.

12. The process as claimed in claim 9, wherein the alcohol is a tertiary alcohol.

13. The process as claimed in claim 9, wherein the solid acid catalyst is added in an amount of about 5 to 30% by weight of the keto ester.

14. The process as claimed in claim 9 wherein the keto ester is a β-keto ester selected from the group consisting of methyl acetoacetate, ethyl acetoacetate, and hexyl acetoacetate.

15. The process as claimed in claim 3 wherein the keto ester is a β-keto ester selected from the group consisting of methyl acetoacetate, ethyl acetoacetate, and hexyl acetoacetate.

16. The process as claimed in claim 3, wherein the alcohol is a tertiary alcohol.

* * * * *